United States Patent [19]

Jirkovsky et al.

[11] 4,169,202
[45] Sep. 25, 1979

[54] PROCESS FOR PREPARING 4,5-DIHYDRO-4-OXOFURAN-2-CARBOXYLIC ACID DERIVATIVES

[75] Inventors: Ivo L. Jirkovsky, Montreal; Dushan Dvornik, Mont Royal; Mitchell N. Cayen, Cote St. Luc, all of Canada

[73] Assignee: American Home Products Corporation, New York, N.Y.

[21] Appl. No.: 912,798

[22] Filed: Jun. 5, 1978

[51] Int. Cl.$^2$ .................. C07D 405/12; C07D 307/68
[52] U.S. Cl. ........................... 546/15; 546/283; 260/347.5; 260/345.8 R; 549/13; 549/60; 549/88; 549/9; 549/1
[58] Field of Search .......... 260/347.5, 347.3, 345.7 R, 260/345.8 R, 327 TH, 327 R, 332.2 A; 546/283, 268, 15

[56] References Cited

U.S. PATENT DOCUMENTS 2,436,532  2/1945  Singleton et al. ................. 260/347.5

OTHER PUBLICATIONS

Fieser & Fieser, Reagents for Organic Synthesis, John Wiley and Sons, Inc. 1963.
R. E. Rosenkranz et al., Helv. Chim. Acta, 46, 1259 (1963).
G. B. Bennett et al., J. Med. Chem. 18, 709 (1976).
G. N. Khabibulina et al., Chem. Abstr. 85, 159951n (1976).

Primary Examiner—Natalie Trousof
Assistant Examiner—Jane T. Fan
Attorney, Agent, or Firm—Arthur E. Wilfond

[57] ABSTRACT

Derivatives of 4,5-dihydro-4-oxofuran-2-carboxylic acid characterized by having two substituents at position 5 and in addition being optionally further substituted at position 3 with a lower alkyl group, as well as esters therefor are disclosed. The foregoing compounds are useful hypolipidemic agents in a mammal. Novel methods for the preparation of these compounds also are disclosed.

6 Claims, No Drawings

PROCESS FOR PREPARING 4,5-DIHYDRO-4-OXOFURAN-2-CARBOXYLIC ACID DERIVATIVES

BACKGROUND OF THE INVENTION a) Field of the Invention

This invention relates to novel derivatives of 4,5-dihydro-4-oxofuran-2-carboxylic acid, to therapeutically acceptable salts thereof, to processes for their preparation, to methods for using the derivatives and to pharmaceutical compositions of the derivatives.

More specifically, the present invention relates to novel derivatives of 4,5-dihydro-4-oxofuran-2-carboxylic acid having two substituents at position 5 and in addition being optionally further substituted at position 3 with a lower alkyl group as well as esters thereof. These derivatives are useful as hypolipidemic agents in a mammal at dosages which do not elicit undesirable side effects.

b) Description of the Prior Art 4,5-Dihydro-4-oxofuran derivatives are extensively described in the literature. Additionally, derivatives of 4,5-dihydro-4-oxofurancarboxylic acids have also been disclosed. For example, 4,5-dihydro-2-methyl-4-oxofuran-3-carboxylic acid and its ethyl ester are described by R. E. Rosenkranz et al., Helv. Chim. Acta., 46, 1259 (1963) and references cited therein. In addition, this reference discloses the structure of 4,5-dihydro-5-methyl-4-oxofuran-2-carboxyic acid as a hypothetical intermediate during the decarboxylation of 4-methoxy-5-methylfuran-2-carboxylic acid. The presence of 4,5-dihydro-5-methyl-4-oxofuran-2-carboxylic acid was not confirmed by isolation or other means.

Recently a few furan derivatives were reported to be hypolipidemic agents. More specifically, some derivatives of 2,3,4,5-tetrahydro-3-oxo-4-hydroxy-iminofurans, 2,5-dihydrofurans and 2,3,4,5-tetrahydrofurans are described to have weak to moderate hypolipidemic activity by G. B. Bennett et al., J. Med. Chem., 19,709(1976). However, the latter report also states that the furan derivatives, disclosed therein, are devoid of a desirable level of hypolipidemic activity.

The 4,5-dihydro-4-oxofuran-2-carboxylic acid derivatives of this invention are novel compounds having hypolipidemic activity without affecting liver weight.

SUMMARY OF THE INVENTION

The compounds of this invention are represented by formula I

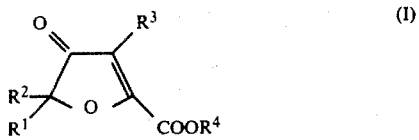

in which $R^1$ and $R^2$ each is lower alkyl, cyclo(lower)alkyl, lower alkoxy (lower)alkylene, phenyl or phenyl mono- or disubstituted with lower alkyl, lower alkoxy, halo, nitro or trifluoromethyl; or $R^1$ and $R^2$ together form a $-(CH_2)_m-X-(CH_2)_n-$ chain wherein m and n each is an integer from one to four and X is methylene, oxa or thia; or $R^1$ and $R^2$ together with the carbon atom to which they are joined form a spiro-[1,2,3,4-tetrahydronaphthalene]-1or spiro[indan]-1-radical; $R^3$ is hydrogen or lower alkyl; and $R^4$ is hydrogen, lower alkyl, cyclo(lower)alkyl, phenyl-(lower)alkylene, amino(lower)alkylene, lower alkylamino(lower)alkylene, di(lower alkyl)amino(lower)alkylene or 3-pyridinyl(lower)alkylene, or a therapeutically acceptable addition salt thereof.

A preferred group of compounds of formua I are those in which $R^1$ is lower alkyl, phenyl or phenyl monosubstituted with halo; $R^2$ is lower alkyl; or $R^1$ and $R^2$ together with the carbon atom to which they are joined form a spiro[1,2,3,4-tetrahydronaphthalene]-1 radical; $R^3$ is hydrogen; and $R^4$ is hydrogen, lower alkyl or 3-pyridinyl(lower)alkylene, or a therapeutically acceptable addition salt thereof.

A most preferred group of compounds of formula I are those in which $R^1$ is lower alkyl, phenyl or 4-chlorophenyl; $R^2$ is lower alkyl; or $R^1$ and $R^2$ together with the carbon atoms to which they are joined form a spiro [1,2,3,4-tetrahydronaphthalene]-1 radical; $R^3$ is hydrogen; and $R^4$ is hydrogen, lower alkyl or 3-pyridinyl methyl, or a therapeutically acceptable addition salt thereof.

The compounds of formula I in which $R^1$, $R^2$, $R^3$ and $R^4$ are as defined herein are prepared by a process, which comprises:

cyclizing a compound of formula X

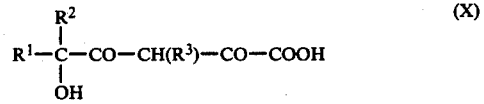

in which $R^1$, $R^2$ and $R^3$ are as defined herein under acidic conditions to obtain the corresponding compound of formula I in which $R^1$, $R^2$, and $R^3$ are as defined herein and $R^4$ is hydrogen, and if desired, esterifying the latter compound of formula I to obtain the corresponding compound of formula I in which $R^1$, $R^2$ and $R^3$ are as defined herein and $R^4$ is lower alkyl, cyclo(lower)alkyl, phenyl(lower)alkylene, amino(lower)alkylene, lower alkylamino(lower)alkylene, di(lower alkyl)amino(lower)alkylene or 3-pyridinyl(lower)alkylene.

More specifically, the compounds of formula I in which $R^1$, $R^2$, $R^3$ and $R^4$ are as defined herein are prepared by a process, which comprises:

reacting a compound of formula II

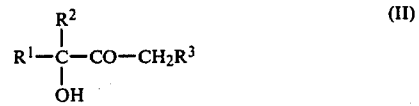

in which $R^1$, $R^2$ and $R^3$ are as defined herein with a di(lower alkyl)oxalate in the presence of a strong inorganic proton acceptor under anhydrous conditions, hydrolyzing the mixture with water at pH 10 to 12, and allowing the latter mixture to stand under acidic conditions to obtain the corresponding compound of formula I in which $R^1$, $R^2$ and $R^3$ are as defined herein and $R^4$ is hydrogen; and if desired esterifying the latter compound of formula I to obtain the corresponding compound of formula I in which $R^1$, $R^2$ and $R^3$ are as defined herein and $R^4$ is lower alkyl cyclo(lower)alkyl,phenyl(lower)alkylene, amino(lower)alkylene, lower alkylamino(lower)alkylene, di(lower alkyl)amino-(lower)alkylene, or 3-pyridinyl(lower)alkylene.

The compounds of formula I, or a therapeutically acceptable addition salt thereof, lower lipid levels in a mammal when administered to said mammal in an effective hypolipidemic amount.

A convenient form for administering the compounds involves a pharmaceutical composition comprising a compound of formula I or a therapeutically acceptable salt thereof and a pharmaceutically acceptable carrier.

DETAILED DESCRIPTION OF THE INVENTION

The term "lower alkyl" as used herein means straight chain alkyl radicals containing from one to six carbon atoms and branched chain alkyl radicals containing three or four carbon atoms and includes methyl, ethyl, n-propyl, isopropyl, n-butyl, isobutyl, n-pentyl, n-hexyl and the like.

The term "lower alkoxy" as used herein means straight chain alkoxy radicals containing from one to six carbon atoms and branched chain alkoxy radicals containing three or four carbon atoms and include a methoxy, ethoxy, isopropoxy, n-butoxy, n-hexyloxy and the like.

The term "lower alkylene" as used herein means a divalent organic radical derived from either straight and branched chain aliphatic hydrocarbons containing from one to six carbon atoms by removal of two hydrogen atoms and includes methylene, ethylene, 1-methylpropylene, 2-methylpropylene, 2-ethylpropylene, 2-butylethylene and the like.

The term "cyclo(lower)alkyl" as used herein means saturated cyclic hydrocarbon radicals containing from three to six carbon atoms and includes cyclopropyl, cyclobutyl, cyclopentyl and cyclohexyl.

The term "lower alkanol" as used herein means both straight and branched chain alkanols containing from one to four carbon atoms and includes methanol, ethanol, isopropanol, butanol and the like. The term "strong inorganic proton acceptor" as used herein means the inorganic bases, preferably the alkali metals, the alkali metal hydrides, amides, hydroxides and alkoxides, for example, sodium, sodium hydroxide, potassium hydroxide, sodium ethoxide, sodium methoxide, sodium hydride and the like.

The term "lower alkanoyl" as used herein means straight chain alkanoyl radicals containing from two to six carbon atoms and a branched chain alkanoyl radical containing four carbon atoms and includes acetyl, propionyl, isobutyryl, n-hexanoyl and the like.

The term "organic proton acceptor" as used herein means the organic bases, or amines for instance, triethylamine, pyridine, N-ethylmorpholine, 1,5-diazabicyclo[4.3.0]non-5-ene and the like.

The term "therapeutically acceptable addition salt" as used herein includes the therapeutically acceptable acid addition salts of the compound of formula I in which $R^4$ is amino(lower)alkylene, lower alkylamino(lower)-alkylene, di(lower alkyl)amino(lower)alkylene or 3-pyridinyl(lower)alkylene. The acid addition salts are prepared by reacting the base form of the appropriate compound of formula 1 with one or more equivalents, preferably with an excess, of the appropriate acid in an organic solvent, for example, diethyl ether or an ethanol-diethyl ether mixture. These salts, when administered to a mammal, possess the same pharmacologic activities as the corresponding bases. For many purposes it is preferable to administer the salts rather than the base compounds. Suitable acids to form these salts include the common mineral acids, for instance hydrohalic, sulfuric or phosphoric acid; as well as the organic acids, for instance, formic, acetic, maleic, malic, ascorbic, succinic, fumaric, citric, or tartaric acid; or acids which are sparingly soluble in body fluids and which impart slow-release properties to their respective salts such as pamoic or tannic acid or carboxymethyl cellulose. The addition salts thus obtained are the functional equivalent of the parent base compound in respect to their therapeutic use. Hence. these addition salts are included within the scope of this invention and are limited only by the requirement that the acids employed in forming the salts be therapeutically acceptable.

Furthermore, the term "therapeutically acceptable addition salt" as used herein also includes the therapeutically inorganic or organic base addition salts of the compound of formula 1 in which $R^4$ is hydrogen, i.e. compound of formula 1 which are acids. These derived salts possess the same activity as the parent acid and are included within the scope of this invention. The acid is transformed in excellent yield into the corresponding therapeutically acceptable salt by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the alkali metals or alkaline earth metals, for example, sodium, potassium, magnesium, calcium and the like. Suitable organic bases include the following amines; lower mono-di- and trialkylamines, the alkyl radicals of which contain up to three carbon atoms, such as methylamine, dimethylamine, trimethylamine, ethylamine, di- and triethylamine, N-methyl-N-ethylamine, and the like; mono-, di and trialkanolamines, the alkanol radicals of which contain up to three carbon atoms, for example, mono- di- and triethanolamine; alkylene-diamines which contain up to six carbon atoms, such as hexamethylenediamine; phenylalkylamines, for example, benzylamine, phenylethylamine and N-methylphenylethylamine; cyclic saturated or unsaturated bases containing up to six carbon atoms, such as pyrrolidine, piperidine, morpholine piperazine and their N-alkyl and N-hydroxyalkyl derivatives, such as N-methyl-m-orpholine and N-(2-hydroxyethyl)-piperidine, as well as pyridine. Furthermore, there may be mentioned the corresponding quaternary salts, such as the tetraalkyl (for example tetramethyl), alkyl-alkanol (for example methyltrimethanol and trimethyl-monoethanol) and cyclic ammonium salts, for example the N-methylpyridinium, N-methyl-N-(2-hydroxyethyl)-morpholinium N,N-dimethylmorpholinium, N-methyl-N-(2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula 1 in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula 1 is dissolved in a suitable solvent of ether moderate or lower polarity, for example, ethanol, methanol, ethyl acetate, diethyl ether and benzene. At least an equivalent amount of the amine corresponding to the desired cation is than added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula 1 with an equivalent amount of the corresponding quaternary ammonium hydroxide in water solution, followed by evaporation of the water.

Also included in this invention are the steroechemical isomers of the compounds of formula I which result from asymmetric centers, contained therein. It is to be understood that the diasteromers arising from such asymmetry are included within the scope of this invention. Such diastereomers are obtained in substantially pure form by classical separation techniques and by sterically controlled synthesis.

Individual enantiomers, which might be separated by fractional crystallization of the diastereomeric salts thereof, are also included.

The compounds of formula 1, or a therapeutically acceptable salt thereof, are useful hypolipidemic agents in a mammal upon oral or parenteral administration. Their hypolipidemic properties are readily demonstrated by the following method: male albino rats (eight rats per group), weighing 140-170g, are given a single daily oral dose of the test compound by gavage as a suspension in 2% Tween-80* in water(1.0 ml). In the same manner, controls are given only 2% Tween-80* in water (1.0 ml) daily. After one week of treatment, animals are decapitated and the blood is collected. The serum is separated by centrifugation and serum cholesterol levels are measured by the method of A. Zlatkis et al., J. Lab. Clin. Med., 41,486(1953), as modified for the autoanalyzer (Method Np-24). Serum phospholipids are determined by the semi-automated technique of M. Kraml, Clin. Chim, Acta., 13,442(1966) and serum triglycerides are measured by the semiautomated method of M. Kraml and L. Cosyns, Clin. Biochem., 2,373(1959). The activity of a test compound is assessed by comparing serum cholesterol, phospholipid and/or triglyceride levels in rats treated with the test compound and control rats and the data are analyzed for significance by the Student's t-test. The following results demonstrating hypotriglyceridemic activity are calculated by subtracting the serum triglyceride level in treated rats from the control serum triglyceride level, and expressing the difference as a percentage of the control level. The following compounds of formula 1 at a dose of 1.0 mmole per kilogram of body weight per day lower triglyceride levels by the indicated percentage: 4,5-dihydro-5-methyl-4-oxo-5-phenylfuran-2-carboxylic acid (42%, described in Example 4),4,5-dihydro-5-(1-methylethyl)-4-oxo-5-phenylfuran-5-carboxylic acid (53%, described in Example 4), 4,5-dihydro-5,5-dimethyl-4-oxofuran-2-carboxylic acid (37%, described in Example 4), spiro[furan-5(4H), 1'(2'H)-naphthalene]-3',4'-dihydro-4-oxo-2-carboxylic acid (43%, described in Example 4), 4,5-dihydro-5-methyl-4-oxo-5-phenylfuran-2-carboxylic acid methyl ester (53%, described in Example 5) and 4,5-dihydro-5-methyl-4-oxo-5-phenylfuran-2-carboxylic acid 3-pyridinylmethyl ester (61%, described in Example 6).

*Trademark

The compounds of formula 1, or a therapeutically acceptable salt thereof, can be used also in combination with known hypolipidemic agents, for example, clofibrate, for reduction of elevated lipids in a mammal. When used in this combination, the compound of formula 1 can be administered sequentially or simultaneously in combination with an effective amount of the know hypolipidemic agent. Suitable methods of administration, compositions and dosages of clofibrate (ATROMID-S) is described by Charles E. Baker, Jr. "Physician's Desk Reference", Medical Economics Company, Oradell, N.J. 1977, pp 593-594, for example, 0.5 to 2.0g per patient per day in divided dosages. , The compounds of formula 1, or a therapeutically acceptable salt thereof, in combination with a known hypolipidemic agent, are used in the same manner as described herein for their use as hypolipidemic agents.

When the compounds of formula 1 of this invention are used as hypolipidemic agents in a mammal, e.g. rats and dogs, they are used alone or in combination with pharmacologically acceptable carriers, the proportion of which is determined by the solubility and chemical nature of the compound, chosen route of administration and standard biological practice. For example, they are administered orally in solid form, e.g. capsule or tablet. They are also administered orally in the form of suspension or solutions, or they may be injected parenterally. For parenteral administration they may be used in the form of a sterile solution containing other solutes, for example, enough saline or glucose to make the solution isotonic.

The tablet compositions for oral administration contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action.

The aqueous suspensions for oral use of the compounds of the invention contain the active ingredient in admixture with one or more non-toxic pharmaceutical excipients, for instance, emulsifying and suspending agents, known to be suitable in the manufacture of aqueous suspensions. Suitable excipients are, for example, methyl-cellulose, sodium alginate, gum acacia, lecithin and so forth. The aqueous suspension can also contain one or more preservatives, one or more colouring agents and/or one or more sweetening agents.

Non-aqueous suspensions for oral use can be formulated by suspending the active ingredient in a vegetable oil, for example, arachis oil, olive oil, seasame oil, or coconut oil; or in mineral oil. The suspension can contain a thickening agent, for example, beeswax, hard paraffin or cetyl alcohol. These compositions can also contain a sweetening agent, flavouring agent and anti-oxidant.

For parenteral administration, which includes intramuscular, intraperitoneal, subcutaneous and intravenous use, the compounds of the invention can be used in the form of a sterile solution, wherein the pH should be suitably adjusted and buffered. The solution can contain other pharmaceutical excipients, for example, enough saline or glucose to make the solution isotonic.

The dosage of a compound of formula 1 of this invention as a hypolipidemic agent will vary with the form of administration and the particular host as well as the age and condition of the host under treatment. Generally, treatment is initiated with small dosages substantially less than the optimal dose of the compound. Thereafter, the dosage is increased by small increments until the optimal effect under the circumstances is reached. In general, a compound of this invention is most desirably administered at a concentration that will generally afford effective results without causing any harmful or deleterious side effects. The effective hypolipidemic amount of the compound usually ranges from about 1.0mg to about 500mg per kilogram of body weight per day, although as aforementioned variations will occur. However, a dosage level that is in the range of from about 5 mg to about 300 mg per kilogram of body weight per day is employed most desirably in order to achieve effective results.

Process

For the preparation of the 4,5-dihydro-4-oxofuran-2-carboxylic acid derivatives of formula I, the preferred starting materials are the α-hydroxyketones of formula II $$R^1-\underset{\underset{OH}{|}}{\overset{\overset{R^2}{|}}{C}}-CO-CH_2R^3 \quad (II)$$

in which $R^1$ and $R^2$ each is lower alkyl, cyclo(lower)alkyl, lower alkoxy (lower)alkylene, phenyl or phenyl mono- or disubstituted with lower alkyl, lower alkoxy, halo, nitro or trifluoromethyl; or $R^1$ and $R^2$ together form a —$(CH_2)_m$—X—$(CH_2)_n$— chain wherein m and n each is an integer from one to four and X is methylene, oxa or thia; or $R^1$ and $R^2$ together with the carbon atom to which they are joined form a spiro[1,2,3,4-tetrahydronaphthalene]-I or spiro[indan]-I radical; and $R^3$ is hydrogen or lower alkyl.

The starting materials of formula II in which $R^1$ and $R^2$ are as defined herein and $R^3$ is hydrogen are either known or they can be prepared as is illustrated in reaction scheme I.

Reaction Scheme I

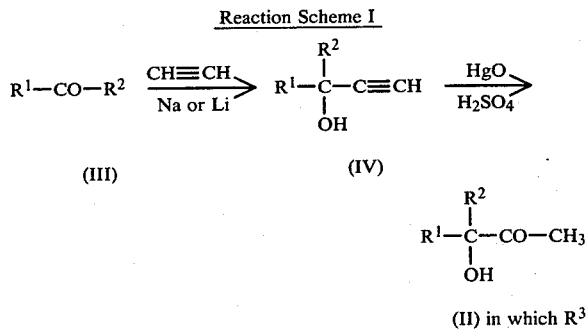

(II) in which $R^3$ is hydrogen

With reference to reaction scheme I, a number of acetylenic carbinols of formula IV are known and commercially available. Alternatively, acetylenic carbinols are readily available from addition of a metallic acetylide to the ketone of formula III in which $R^1$ and $R^2$ are as defined herein using the method described by A. W. Johnson, Acetylenic Compounds, Vol. 1, The Acetylenic Alcohols, E. Arnold Co, London, 1946; R. a. Raphael, Acetylenic Compounds in Organic Synthesis, London, Butterworth's Sc. Publ., 1955; P. A. Robins and J. Walker, J. Chem. Soc., 177(1957); and E. D. Bergmann et al., J. Appl. Chem. 3,39(1953). In the preferred method, a mixture of the compound of formula III and lithium or sodium in a solution of anhydrous liquid ammonia saturated with gaseous acetylene is allowed to react for nine hours and the corresponding compound of formula IV is isolated.

The acetylenic carbinols of formula IV are converted to the corresponding α-hydroxyketones of formula II, by hydration of the acetylenic carbinol in a mixture of mercuric oxide(red form) or mercuric sulfate, aqueous tetrahydrofuran and sulfuric acid at 60°–65° C. for one to six hours, according to the procedure described by A. W. Johnson, cited above, pp 102–105; E. D. Bergmann and D. F. Herman, J. Appl. Chem., 3,42(1953), G. F. Hennian and B. R. Fleck, J. Amer. Chem. Soc., 77,3253(1955); and G. F. Hennian and E. J. Watson, J. Org. Chem., 23,656(1958).

The starting materials of formula II in which $R^1$ and $R^2$ are as defined herein and $R^3$ is lower alkyl are either known or they can be prepared as is illustrated in reaction scheme 2.

Reaction Scheme 2

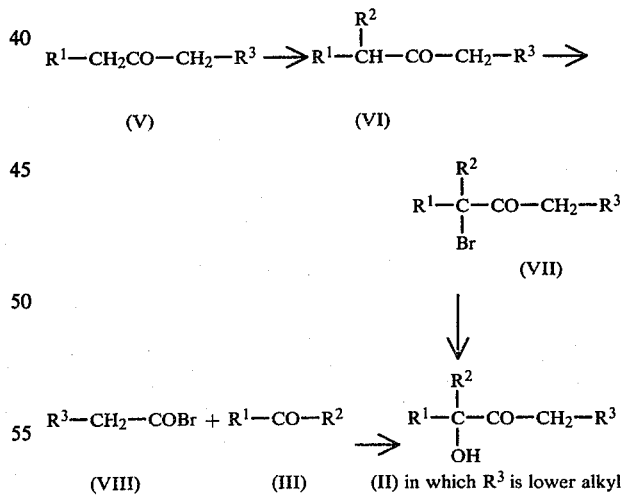

With reference to reaction scheme 2, an organometallic derivative of the compound of formula VIII is condensed with the ketone of formula III to obtain the corresponding α-hydroxyketone of formula II in which $R^3$ is lower alkyl according to the conditions described by I. I. Lapkin and T. N. Povarnitsyna, Zh. Obshch. Khim. 38,99(1968), cf. Chem. Abstr., 69,19233z.

The alternative route starting from the compound of formula V is especially suitable for preparing the α-keto alcohols of formula II in which $R^1$ or $R^2$ is phenyl or phenyl mono- or disubstituted with lower alkyl, lower alkoxy, halo, nitro or trifluoromethyl. Alkylation of the compound of formula V, using the method of K. Binovic and S. Vrancea, Chem. Ther., 313(1968), gives the corresponding compound of formula VI. The latter compound is brominated, according to the conditions described by J. R. Catch et al., J. Chem. Soc. 272(1948), to obtain the corresponding bromo-ketone of formula VII. Conversion of the latter bromoketone to the corresponding α-hydroxyketone of formula II is described by J. G. Aston and R. B. Greenberg, J. Amer. Chem. Soc., 62,2590(1940); J. Kapron and J. Wiemann, Bull. Soc. Chim. France, 12,945(1945); and Y. L. Pascal, Ann. Chim. (Paris), 245(1968).

In addition to the above described preparations, α-hydroxyketones of formula II can be prepared by methods described by Y. L. Pascal, cited above, and P. Kaufmann, J. Amer. Chem. Soc., 26,5794(1954).

Reaction scheme 3 illustrates the conversion of the α-hydroxyketone of formula II to the corresponding compound of formula I in which $R^1$, $R^2$ and $R^3$ are as defined herein.

an aqueous solution of a water miscible organic solvent, preferably methanol, ethanol, tetrahydrofuran or dioxane, at 15° to 30° C. for 15 to 40 hours. The latter solution is extracted with a water immiscible organic solvent, preferably diethyl ether, benzene, chloroform, dichloromethane and the like, and the extract is evaporated to obtain the corresponding compound of formula X.

The latter compound is cyclized under acidic conditions to obtain the corresponding compound of formula I in which $R^1$, $R^2$ and $R^3$ are as defined herein and $R^4$ is hydrogen. In one method of achieving this cyclization, a solution of the compound of formula X and 0.1 to 10 molar equivalents, preferably 0.1 to 0.4 molar equivalents, and an acid catalyst, for example, hydrogen chloride, hydrogen bromide, hydrochloric acid, hydrobromic acid, p-toluenesulfonic acid, sulfuric acid, phosphoric acid, polyphosphoric acid and the like, preferably p-toluenesulfonic acid or hydrogen chloride, in an inert organic solvent, preferably benzene or toluene, is maintained at 20° to 100° C. for two to 50 hours. Alternatively, the compound of formula X is cyclized in an

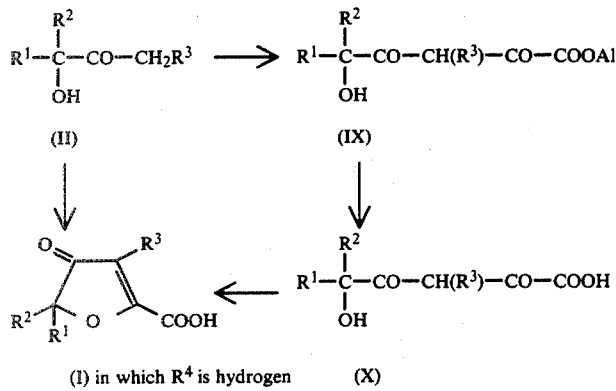

As illustrated by reaction scheme 3, the compound of formula I in which $R^4$ is hydrogen is prepared from the compound of formula II via the route II→IX→X→I. Although the intermediates of formula IX and X can be isolated and further reacted in separate steps, the compound of formula II can be converted to the corresponding compound of formula I via intermediates IX and X in a single reaction vessel without isolating the latter intermediates.

The first step in the conversion of the α-hydroxyketone of formula II is the condensation of substantially equimolar amounts of the α-hydroxyketone and a di(-lower alkyl)oxalate, preferably dimethyl or diethyl oxalate, in the presence of one to four molar equivalents of a strong inorganic proton acceptor, preferably sodium hydride, in an anhydrous inert organic solvent. Preferred inert organic solvents can be selected from the di(lower alkyl)ethers or cyclic ethers, for example, diethyl ether, dioxane and tetrahydrofuran. The reaction mixture is maintained at 30° to 70° C., preferably 50° to 60° C., for 10 to 30 hours. The resultant enolate salt is filtered as rapidly as possible, dissolved in water, acidified with a diluted inorganic acid, and the corresponding compound of formula IX is extracted with an inert water immiscible organic solvent, preferably diethyl ether.

Hydrolysis of the latter compound is readily achieved under alkaline conditions with a solution of one to three molar equivalents of potassium or sodium hydroxide in aqueous solution containing the acid catalyst at 10° to 50° C. for 10 to 50 hours. Preferred acid catalysts for use in the aqueous conditions can be selected from hydrochloric acid, sulfuric acid, hydrobromic acid and phosphoric acid. The aqueous solution usually requires sufficient acid catalyst so that the solution is maintained at pH 0.5 to 3.0 preferably 1.0 to 2.0.

In a modification of the conversion of the compound of formula II to the corresponding compound of formula I, the above individual steps of condensation, alkaline hydrolysis and cyclization are combined in a process wherein the intermediates of formula IX and X are not isolated.

In this modification, the α-hydroxyketone of formula II is condensed with a di(lower alkyl) oxalate in the same manner as described above. However, the reaction mixture is not filtered but instead is mixed with about an equal volume of water. The resulting aqueous alkaline solution is, if required, adjusted to pH 10 to 12 with sodium hydroxide and maintained at pH 10 to 12 and at 15° to 30° C. for 10 or 40 hours and washed with a water immiscible organic solvent, preferably diethyl ether or benzene. An acid catalyst, preferably hydrochloric acid, hydrobromic acid, sulfuric acid or phosphoric acid, is added to the aqueous solution until the solution reaches pH 0.5 to 3.0, preferably 1.0 to 2.0. The acidic solution is maintained at 10° to 50° C., preferably 20° to 30° C., for 0.5 to 10 hours and extracted with a water immiscible organic solvent, for example, ethyl acetate, diethyl ether, benzene, toluene chloroform, dichloromethane and the like. The organic extract is evaporated and, if required, purified to obtain the corresponding compound of formula I in which $R^4$ is hydrogen.

If the aqueous alkaline solution in the latter preparation is maintained at pH 8 to 9 instead of pH 10 to 12, a corresponding intermediate of formula XI

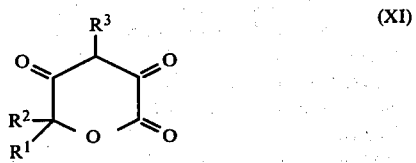

(XI)

in which $R^1$, $R^2$ and $R^3$ are as defined herein is isolated after acidification of the aqueous alkaline solution. More specifically, the α-hydroxyketone of formula II is condensed with a di(lower alkyl) oxalate in the same manner as described above. The reaction mixture is not filtered but instead is mixed with about an equal volume of water and if necessary the resulting aqueous solution is adjusted to pH 8 to 9 with dilute hydrochloric acid or sodium hydroxide. The resulting aqueous solution is maintained at pH 8 to 9 and at 15° to 30° C. for one to five hours and washed with a water immiscible organic solvent, in the same manner as described above. The mixture is acidified, maintained at 10° to 50° C., preferably 20° to 30° C., for one to 30 minutes and extracted, in the same manner as described above for 11→1, to obtain the corresponding intermediate of formula XI.

Reaction of the intermediate of formula XI under aqueous alkaline conditions at pH 10 to 12 gives the corresponding compound of formula I in which $R^4$ is hydrogen. For this reaction, a solution of the compound of formula II in aqueous potassium or sodium hydroxide is maintained at pH 10 to 12 and at 15° to 30° C. for 10 to 40 hours and washed with a water immiscible organic solvent, in the same manner as described above. Subsequently, acidification of the aqueous solution, maintenance of the acidic solution and extraction, in the same manner as described above for 11→1, gives the corresponding compound of formula I in which $R^4$ is hydrogen.

The acidic compound of formula I in which $R^4$ is hydrogen is esterified to obtain the corresponding ester of formula I in which $R^4$ is lower alkyl, cyclo(lower)alkyl, phenyl(lower)alkylene, amino(lower)alkylene, lower alkylamino(lower)alkylene, di(lower alkyl)amino(lower)alkylene or 3-pyridinyl(lower)alkylene. A number of esterification methods can be used, for example, mixed anhydride; dehydrative coupling reagents, for instance, dicyclohexylcarbodiimide; acid catalysts; diazoalkanes; and acid chloride.

A preferred method of esterification employs an acid catalyst, preferably 0.1 to 1.0 molar equivalents of anhydrous sulfuric acid or hydrogen chloride, and 2 to 50 equivalents of a lower alkanol, hydroxycyclo(lower)alkane, phenyl(lower)alkanol, amino(lower)alkanol, lower alkylamino(lower)alkanol, di(lower alkyl)amino(lower)alkanol or 3-pyridinyl(lower)alkanol at 50° to 100° C. for one to ten hours. It should be noted that when amino(lower)alkanol, lower alkylamino(lower)alkanol, di(lower alkyl)amino(lower)alkanol or 3-pyridinyl(lower)alkanol is used, then a corresponding additional molar mount of the acid catalyst should be present in the reaction vessel. If the reactants are mutually soluble, a solvent for the esterification can be omitted. Otherwise, any anhydrous inert organic solvent can be used, for example, dimethylformamide, benzene, toluene, chloroform and the like.

Another preferred method of esterification proceeds through the acid chloride. In this method, a solution of the acidic compound of formula I in which $R^4$ is hydrogen and 5 to 50 molar equivalents of thionyl chloride is heated at 50° to 80° C. for one to ten hours and evaporated to obtain the corresponding acid chloride. A solution of the latter acid chloride, one to ten molar equivalents of the above noted alcohols and an organic proton acceptor, for example, pyridine or triethylamine, in an inert organic solvent, for example, acetone, benzene, dichloromethane, toluene, chloroform or dimethylformamide, preferably acetone, is maintained at 0° to 50° C. for to two to ten hours. Evaporation and purification affords the compound of formula I in which $R^1$, $R^2$ and $R^3$ are as defined herein and $R^4$ is lower alkyl, cyclo(lower)alkyl, phenyl(lower)alkylene, amino(lower)alkylene, lower alkylamino(lower)alkylene, di(lower alkyl)amino(lower)alkylene or 3-pyridinyl(lower)alkylene.

The following examples illustrate further this invention.

EXAMPLE 1

3-Hydroxy-4-methyl-3-phenyl-1-pentyne
(IV:$R^2$=CH(CH$_3$)$_1$ and $R^2$=Ph)

A reaction flask, equipped with a dry-ice reflux condenser, is charged with 700 ml of freshly condensed liquid ammonia. The ammonia gas is passed through a tower of potassium hydroxide pellets. Upon stirring, a rapid stream of acetylene gas (dried in a sulfuric acid wash bottle) is introduced into the ammonia for 10 min, then the rate of passage of the acetylene is reduced and a continuous flow of acetylene through the reaction mixture is maintained during the following operations (approx. 9 hr). Small pieces of sodium (9.2 g) are inserted, and 2 hr later, 2-methyl-1-phenyl-1-propanone (50 g) is added dropwise. The stirring is continued for 6 hr at −33° C. then, the stream of acetylene is shut off, and the ammonia is allowed to evaporate in the hood (overnight). After adding cautiously ice-water, the resultant solution is acidified with diluted sulfuric acid, and extracted with diethyl ether. The combined extracts are washed with saturated brine, dried over magnesium sulfate, filtered, and evaporated to yield 45.5 g of the title compound, ir (CHCl$_3$) 3600, 3310, 1450, and 1010 cm$^{-1}$ and nmr (CDCl$_3$) δ 0.85 and 1.07 (d), 2.10(heptuplet), 2.35(s), 2.66(s), 7.27(m) and 7.55(m).

EXAMPLE 2

3-Hydroxy-4-methyl-3-phenyl-2-pentanone
(II:$R^2$=CH(CH$_3$)$_2$, $R^1$=Ph and $R^3$=H)

To a refluxing mixture of tetrahydrofuran (70 ml), water (5 ml), and conc. sulfuric acid (1.5 g) is added 1 g of red mercuric oxide and the reflux is continued for 5 min. Then, the inside temperature is adjusted to 60°–62° C. and 10 g of 3-hydroxy-4-methyl-3-phenyl-1-pentyne (described in Example 1) is added. The reaction is exothermic (spontaneous mild reflux) and there is a noticeable clearing of the mixture. Another 1 g of mercuric oxide is added, and the solution is refluxed for 30 min. The reaction mixture is stirred at 60° C. for an additional 3 hr, during which time the precipitation of a mercury sludge occurred. After cooling, the slurry is diluted with 100 ml of diethyl ether and filtered through diatomaceous earth. The filter cake is washed with 200 ml of diethyl ether, and the combined filtrates are washed repeatedly with water, dried over magnesium sulfate, filtered, and evaporated to give 10.6 g of the title product, ir (CDCl$_3$) 3470 and 1715-1710 cm$^{-1}$ and nmr (CDCl$_3$) δ 0.91(d), 2.15(s), 2.79(heptuplet), 4.39(s) and 7.20–7.65(m).

EXAMPLE 3

3-Hydroxy-3-phenyl-2-butanone(II: $R^2$=Me, $R^1$=Ph and $R^3$=H).

The title compound is prepared by using a modified method of G. F. Hennion and B. R. Fleck, J. Amer. Chem. Soc., 77,3258(1955). To a mixture of methanol (5 ml), water (0.2 ml), sulfuric acid (100 mg), and mercuric sulfate (100 mg) is added at 55° C. a solution of 3-hydroxy-3-phenyl-1-butyne (2 g) in 90% aqueous methanol (5 ml) over a period of 90 min. The reaction is slightly exothermic, and the inside temperature is maintained at 55°–57° C. During the reaction time, 50 mg of mercuric sulfate is added. When addition of the acetylenic component is complete, another portion (50 mg) of mercuric sulfate is added, and the mixture is stirred at 55° C. for 1 hour. During this time 1 ml of water is added. After cooling, the reaction mixture is poured into ice-water and extracted with diethyl ether. The combined extracts are washed with water, dried over magnesium sulfate, filtered and evaporated. The resultant oil is chromatographed on silica gel using benzene. The appropriate eluates are evaporated to give 0.5g of the title compound, ir(CHCl$_3$)3450 and 1741 cm$^{-1}$ and nmr(CDCl$_3$) δ 1.75(s), 2.08(s), 4.50(s) and 7.40(m).

In the same manner but replacing 3-phenyl-3-hydroxy-1-butyne with an equivalent amount of 3-hydroxy-3-(4-chlorophenyl)-1-butyne, 3-hydroxy-3-methyl-1-butyne, 1-ethynyl-1,2,3,4-tetrahydronaphthalene, 3-ethyl-3-hydroxy-1-heptyne, 3-hydroxy-3, 3-diphenyl-1-propyne, 3-cyclohexyl-3-hydroxy-1-hexyne, 4-ethoxy-3-(3-methoxyphenyl)-3-hydroxy-1-butyne, 3-(3,4-diethylphenyl)-3-hydroxy-3-(4-nitrophenyl)-1-propyne, 3-ethynyl-3-hydroxytetrahydrofuran, 1-ethynyl-1-hydroxycyclohexane, 1-ethynyl-1-hydroxyindane or 3-cyclopentyl-5-ethoxy-3-hydroxy-1-pentyne, the following compounds of formula II are obtained, respectively: 3-hydroxy-3-(4-chlorophenyl)-2-butanone, ir (CHCl$_3$)3440 and 1710 cm$^{-1}$, 3-hydroxy-3-methyl-2-butanone, 1-acetyl-1-hydroxy-1,2,3,4-tetrahydronaphthalene ir(film) 3450 and 1710 cm$^{-1}$, 3-ethyl-3-hydroxy-2-heptanone, 3-hydroxy-3,3-diphenyl-2-propanone, 3-cyclohexyl-3-hydroxy-2-hexanone, 4-ethoxy-3-(3-methoxyphenyl)-3-hydroxy-2-butanone, 3-(3,4-diethylphenyl)-3-hydroxy-3-(4-nitrophenyl)-2-propanone, 3-acetyl-3-hydroxytetrahydrofuran, 1-acetyl-1-hydroxycyclohexane, 1-acetyl-1-hydroxyindane and 3-cyclopentyl-5-ethoxy-3-hydroxy-2-pentanone.

EXAMPLE 4

4,5-Dihydro-5-methyl-4-oxo-5phenylfuran-2-carboxylic acid (I:$R^2$=Me, $R^1$=Ph, and $R^3$ and $R^4$=H)

To a stirred suspension of sodium hydride (10.5 g, 54% in mineral oil) in dry tetrahydrofuran (400 ml) is added dropwise a solution of diethyl oxalate (16 g) and 3-hydroxy-3-phenyl-2-butanone (16.4 g described in Example 3) in tetrahydrofuran (50 ml). The solution temperature is maintained at 55°–60° C., and the solution is maintained at this temperature for 18 hr after the addition is complete. The cold reaction mixture is poured into water, the mixture is adjusted to pH 11 with sodium hydroxide and allowed to stand for 24 hours, and washed with diethyl ether. Upon addition of 6N hydrochloric acid, the aqueous solution is adjusted to pH 1. The acidic mixture is kept at 20° to 30° C. for 2 hours and extracted with diethyl ether. The ether extract is dried and slowly evaporated to obtain crystals (20 g) of the title compound, mp 174°–176° C.

ANAL: Calculated for $C_{12}H_{10}O_4$: C, 66.06; H, 4.62%: Found: C, 66,41; H,4.69%.

A solution of the title compound in diethyl ether and a solution of an equimolar amount of benzylamine in diethyl ether are mixed at 0° C. The precipitate is collected by filtration and crystallized from isopropanol to obtain the benzylamine salt of the title compound mp 192°–193° C.

In the same manner but replacing 3-hydroxy-3-phenyl-2-butanone with an equivalent amount of another compound of formula II described in Example 2 and 3, the following compounds of formula I are obtained, respectively: 4,5-dihydro-5-(1-methylethyl)-4-oxo-5-phenylfuran-2-carboxylic acid, mp 151°–153° C. and nmr (CDCl$_3$) δ0.77(d), 1.01(d), 2.85(heptuplet) 6.03(s), 6.45(s) and 7.33(m); 5-(4-chlorophenyl)-4,5-dihydro-5-methyl-4-oxofuran-2-carboxylic acid, mp 169° C. and nmr (CDCl$_3$) δ1.75(s), 6.25(s) and 7.45(m); 4,5-dihydro-5,5-dimethyl-4-oxofuran-2-carboxylic acid, mp 180°–181° C. and ir (nujol) 2800(broad), 1737, 1670 and 1600 cm$^{-1}$; spiro[furan-5(4H), 1'(2'H)-naphthalene]-3',4'-dihydro-4-oxo-2-carboxylic acid, mp 152°–154° C. and nmr (MeOH-d$_4$) δ2.07(m), 2.84(t), 6.29(s) and 6.8–7.4(m); 5-butyl-5-ethyl-4,5-dihydro-4-oxofuran-2-carboxylic acid; 4,5-dihydro-4-oxo-5,5-diphenylfuran-2-carboxylic acid; 5-cyclohexyl-4,5-dihydro-4-oxo-5-propylfuran-2-carboxylic acid; 4,5-dihydro-5-ethoxymethyl-5-(3-methoxyphenyl)-4-oxofuran-2-carboxylic acid; 4,5-dihydro-5-(3,4-diethylphenyl)-5-(4-nitrophenyl)-4-oxofuran-2-carboxylic acid; 1,7-dioxaspiro[4,4]non-2-ene-4-oxo-2-carboxylic acid; 1-oxaspiro[4,5]dec-2-ene-4-oxo-2-carboxylic acid; spirop[furan-5(4H), 1'-indan]-4-oxo-2-carboxylic acid; and 5-cyclopentyl-4,5-dihydro-5-(3-ethoxypropyl)-4-oxofuran-2-carboxylic acid.

EXAMPLE 5

4,5-Dihydro-5-methyl-4-oxo-5-phenylfuran-2-carboxylic Acid Methyl Ester (I: $R^2$ and $R^4$=Me, $R^1$=Ph and $R^3$=H)

A mixture of 4,5-dihydro-5-methyl-4-oxo-5-phenylfuran-2-carboxylic acid (0.4 g, described in Example 4), absolute methanol (50 ml), and sulfuric acid (3 drops) is refluxed overnight and evaporated. The residue is diluted with 50 ml of diethyl ether, and the solution is washed quickly with saturated sodium bicarbonate and water, dried over magnesium sulfate, filtered, and evaporated. The residue is crystallized from diethyl ether to obtain the title compound (0.32 g) mp 60°–62° C. and nmr (CDCl$_3$) δ1.81(s), 3.99(s), 6.25(s) and 7.42(m).

In the same manner but replacing methanol with an equivalent amount of ethanol, propanol or butanol, the following compounds of formula I are obtained, respectively: 4,5-dihydro-5-methyl-4-oxo-5-phenylfuran-2-carboxylic acid ethyl ester, 4,5-dihydro-5-methyl-4-oxo-5-phenylfuran-2-carboxylic acid propyl ester and 4,5-dihydro-5-methyl-4-oxo-5-phenylfuran-2-carboxylic acid butyl ester.

Similarly, but replacing 4,5-dihydro-5-methyl-4-oxo-5-phenylfuran-2-carboxylic acid with an equivalent amount of another compound of formula I described in Example 4, the following compounds of formula I are obtained, respectively: 4,5-dihydro-5-(1-methylethyl)-4-oxo-5-phenylfuran-2-carboxylic acid methyl ester; 5-(4-chlorophenyl)-4,5-dihydro-5-methyl-4-oxofuran-2-carboxylic acid methyl ester; 4,5-dihydro-5,5-dimethyl-4-oxofuran-2-carboxylic acid methyl ester, mp 66° C., ir(CHCl$_3$)1720, 1695 and 1575 cm$^{-1}$; spiro[furan-5(4H),1'(2'H)-naphthalene]-3',4'-dihydro-4-oxo-2-carboxylic acid methyl ester; 5-butyl-5-ethyl-4,5-dihydro-4-oxofuran-2-carboxylic acid methyl ester; 4,5-dihydro-4-oxo-5,5-diphenylfuran-2-carboxylic acid methyl ester; 5-cyclohexyl-4,5-dihydro-4-oxo-5-propylfuran-2-carboxylic acid methyl ester; 4,5-dihydro-5-ethoxymethyl-5-(3-methoxyphenyl)-4-oxofuran-2-carboxylic acid methyl ester; 4,5-dihydro-5-(3,4-diethylphenyl)-5-(4-nitrophenyl)-4-oxofuran-2-carboxylic acid methyl ester; 1,7-dioxaspiro[4,4]non-2-ene-4-oxo-2-carboxylic acid methyl ester; 1-oxaspiro[4,5]dec-2-ene4-oxo-2-carboxylic acid methyl ester; spiro[furan-5-(4H),1'-indan]-4-oxo-2-carboxylic acid methyl ester; and 5-cyclopentyl-4,5-dihydro-5-(3-ethoxypropyl)-4-oxofuran-2-carboxylic acid methyl ester.

EXAMPLE 6

4,5-Dihydro-5-methyl-4-oxo-5-phenylfuran-2-carboxylic Acid 3Pyridinylmethyl Ester (I: $R^2$=Me, $R^1$=Ph, $R^3$=H and $R^4$=3-pyridinylmethyl).

A mixture of 4,5-dihydro-5-methyl-4-oxo-5-phenylfuran-2-carboxylic acid (8.75 g, described in Example 4) and thionyl chloride (90 ml) is refluxed for 3 hr and evaporated. The residue is dissolved in benzene (100 ml) and evaporated (twice). The infrared spectrum of the residue is indicative of a quantitative conversion of the carboxylic acid into the carbonyl chloride, ir (CHCl$_3$) 1820 and 1795, 1755 and 1715 cm$^{-1}$. This material is dissolved in 50 ml of dry acetone and added to a mixture of 3-pyridinemethanol (4.8 g), pyridine (3.1 g), and acetone (100 ml) at 0° C. The reaction mixture is stirred at 20° to 30° C. temperature for 4 hr and evaporated under reduced pressure. The residue is partitioned between chloroform and saturated sodium bicarbonate. The organic phase is collected, dried and evaporated to give 8.8 g of the title compound, ir (CHCl$_3$) 1753, 1742, 1715(broad), 1595 and 1100 cm$^{-1}$ and nmr (CDCl$_3$) δ1.78(s), 5.45(s), 6.29(s), 7.42(m), 7.84(doublet of triplets) and 8.60(m).

The title compound (18 g) is dissolved in acetone (20 ml) and a solution of hydrogen chloride in diethyl ether is added until precipitation is complete. The solvent is decanted and the residue is triturated with diethyl ether. The residue is crystallized from acetone to obtain the hydrochloride salt (15 g) of the title compound, mp 124°-125° C.

ANAL: Calculated for C$_{18}$H$_{15}$NO$_4$.HCl: C,62.52; H,4.66; N,4.05%; Found: C,62.30; H,4.53; N,3.94%.

A solution of the title compound in diethyl ether and a solution of a half molar equivalent of (E)-2-butenedioic acid in isopropanol are combined at −10° C. The resulting precipitate is filtered and crystallized from acetonitrile to obtain the hemi-(E)-2-butenedioate salt, mp 128°-130° C., of the title compound.

In the same manner but replacing 4,5-dihydro-5-methyl-4-oxo-5-phenylfuran-2-carboxylic acid with an equivalent amount of another compound of formula I described in Example 4, the following compounds of formula I are obtained, respectively:
4,5-dihydro-5-(1-methylethyl)-4-oxo-5-phenylfuran-2-carboxylic acid 3-pyridinylmethyl ester; 5-(4-chlorophenyl)-4,5-dihydro-5-methyl-4-oxofuran-2-carboxylic acid 3-pyridinylmethyl ester, nmr(CDCl$_3$)δ1.77(s), 5.46(s), 6.29(s), 7.42(m), 7.86(m) and 8.70(m); 4,5-dihydro-5,5-dimethyl-4-oxofuran-2-carboxylic acid 3-pyridinylmethyl ester, mp 109°-110° C.; spiro[furan-5(4H),-1'(2'H)-naphthalene]-3',4'-dihydro-4-oxo-2-carboxylic acid 3-pyridinylmethyl ester; 5-butyl-5-ethyl-4,5-dihydro-4-oxofuran-2-carboxylic acid 3-pyridinylmethyl ester; 4,5-dihydro-4-oxo-5,5-diphenylfuran-2-carboxylic acid 3-pyridinylmethyl ester; 5-cyclohexyl-4,5-dihydro-4-oxo-5-propylfuran-2-carboxylic acid 3-pyridinylmethyl ester; 4,5-dihydro-5-ethoxymethyl-5-(3-methoxyphenyl)-4-oxofuran-2-carboxylic acid 3-pyridinylmethyl ester; 4,5-dihydro-5-(3,4-diethylphenyl)-5-(4-nitrophenyl)-4-oxofuran-2-carboxylic acid 3-pyridinylmethyl ester; 1,7-dioxaspiro[4,4]non-2-ene-4-oxo-2-carboxylic acid 3-pyridinylmethyl ester; 1-oxaspiro[4,5]dec-2-ene-4-oxo-2-carboxylic acid 3-pyridinylmethyl ester; spiro[furan-5(4H), 1'-indan]-4-oxo-2-carboxylic acid 3-pyridinylmethyl ester; and 5-cyclopentyl-4,5-dihydro-5-(3-ethoxypropyl)-4-oxofuran-2-carboxylic acid 3-pyridinylmethyl ester.

EXAMPLE 7

6-Methyl-6-phenyltetrahydropyran-2,3,5-trione (XI: $R^2$=Me, $R^1$=Ph and $R^3$=H)

To a stirred suspension of sodium hydride (10.5 g 54% in mineral oil) in dry tetrahydrofuran (400 ml) is added dropwise a solution of diethyl oxalate (16 g) and 3-hydroxy-3-hydroxy-3-phenyl-2-butanone ( 16.4 g described in Example 3) in tetrahydrofuran (50 ml). The solution temperature is maintained at 55°-60° C., and the solution is maintained at this temperature for 18 hr after the addition is completed. The cold reaction mixture is poured into water and the mixture is adjusted pH 8 to 9 with sodium hydroxide or hydrochloric acid. This mixture at pH 8 to 9 is allowed to stand for 24 hr and extracted with diethyl ether. The ether extract is dried, evaporated and crystallized from diethyl ether to obtain the title compound: mp 142°-144° C.; ir (nujol) 3130, 1718 and 1640 cm$^{-1}$; uv (MeOH) λ$_{max}$ 268 nm (ϵ=8830) and nmr (MeOH-d$_3$) δ1.89 (s), 5.92 (s) and 7.34 (s).

Anal. Calc'd for C$_{12}$H$_9$O$_4$: C, 66.05; H, 4.62% Found: C, 66.14; H, 4.83%.

EXAMPLE 8

4,5-Dihydro-5-methyl-4-oxo-5-phenylfuran-2-carboxylic acid (1:$R^2$=Me, $R^1$=Ph, and $R^3$ and $R^4$=H)

A mixture of 6-methyl-6-phenyltetrahydropyran-2,3,5-trione (2.18 g, described in Example 7) in aqueous sodium hydroxide (15 ml) at pH 11 is stirred for 24 hr and washed with diethyl ether. Hydrochloric acid (6N) is added until the solution becomes acidic at pH 1 to 4. The precipitate is collected and crystallized from diethyl ether to obtain the title compound (2.0 g), mp 174°-176° C.

We claim:

1. A process for preparing a compound of formula 1

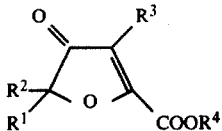

in which $R^1$ and $R^2$ each is lower alkyl, cyclo(lower)alkyl, lower alkoxy(lower)alkylene, phenyl or phenyl mono- or disubstituted with lower alkyl, lower alkoxy, halo, nitro or trifluoromethyl; or $R^1$ and $R^2$ together form a —$(CH_2)_m$—X—$(CH_2)_n$— chain wherein m and n each is an integer from one to four and X is methylene, oxa or thia; or $R^1$ and $R^2$ together with the carbon atom to which they are joined form a spiro[1,2,3,4-tetrahydronaphthalene]-1 or spiro-[indan]-1 radical; $R^3$ is hydrogen or lower alkyl; and $R^4$ is hydrogen, lower alkyl, cyclo(lower)alkyl, phenyl(lower)alkylene, amino(lower)alkylene, lower alkylamino(lower)alkylene, di(lower alkyl)amino(lower)alkylene or 3-pyridinyl(lower)alkylene, which comprises:

reacting a compound of formula 11

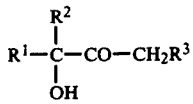

in which $R^1$, $R^2$ and $R^3$ are as defined herein with a di(lower alkyl) oxalate in the presence of a strong inorganic proton acceptor under anhydrous conditions, hydrolyzing the mixture with water at about pH 10 to about pH 12, and allowing the latter mixture to stand under acidic conditions to obtain the compound of formula 1 in which $R^1$, $R^2$ and $R^3$ are as defined herein and $R^4$ is hydrogen; and if desired, esterifying the latter compound of formula 1 to obtain the corresponding compound of formula 1 in which $R^1$, $R^2$ and $R^3$ are as defined herein and $R^4$ is lower alkyl, cyclo(lower)alkyl, phenyl(lower)alkylene, amino(lower)alkylene, lower alkylamino(lower)alkylene, di(lower alkyl)amino(lower)alkylene or 3-pyridinyl(lower)alkylene.

2. A process according to claim 1, wherein $R^1$ is lower alkyl, phenyl or phenyl monosubstituted with halo; $R^2$ is lower alkyl; or $R^1$ and $R^2$ together with the carbon atom to which they are joined form a spiro[1,2,3,4-tetrahydronaphthalene]-1 radical; $R^3$ is hydrogen and $R^4$ is hydrogen, lower alkyl or 3-pyridinyl(lower)alkylene.

3. A process, as claimed in claim 1, wherein acidic conditions is obtained by the addition of hydrochloric acid, hydrobromic acid, sulfuric acid, phosphoric acid or polyphosphoric acid.

4. A process, as claimed in claim 1, wherein said strong inorganic proton acceptor is sodium hydride.

5. A process, as claimed in claim 1, wherein said di(lower alkyl) oxalate is selected from dimethyl oxalate or diethyl oxalate.

6. The process of claim 1 for the synthesis of a therapeutically acceptable addition salt of said compound of formula 1 in which $R^1$, $R^2$ and $R^3$ are as defined therein and $R^4$ is hydrogen, amino(lower)alkylene, lower alkylamino(lower)alkylene, di(lower alkyl)amino(lower)alkylene or 3-pyridinyl(lower)alkylene, wherein said compound of formula 1 in which $R^1$, $R^2$ and $R^3$ are as defined herein and $R^4$ is hydrogen is reacted with a therapeutically acceptable organic or inorganic base to obtain the corresponding thereapeutically acceptable organic or inorganic base addition salt of said compound of formula 1 in which $R^1$, $R^2$ and $R^3$ are as defined herein and $R^4$ is hydrogen; or said compound of formula 1 in which $R^1$, $R^2$ and $R^3$ are as defined herein and $R^4$ is amino(lower)alkylene, lower alkylamino(lower)alkylene, di(lower alkyl)amino(lower)alkylene or 3-pyridinyl(lower)alkylene is reacted with a therapeutically acceptable acid to obtain the corresponding therapeutically acceptable acid addition salt of said compound of formula 1 in which $R^1$, $R^2$ and $R^3$ are as defined herein and $R^4$ is amino(lower)alkylene, lower alkylamino(lower)alkylene, di(lower alkyl)amino(lower)alkylene or 3-pyridinyl(lower)alkylene.

* * * * *